United States Patent [19]

Bouton et al.

[11] Patent Number: 4,927,975

[45] Date of Patent: May 22, 1990

[54] PROCESS FOR PREPARING CERTAIN DECAHYDRO-7H-3-OL-7-ONES

[75] Inventors: Marie-Madeleine Bouton; Jean Jacques, both of Paris; André Pierdet, Noisy-Le-Sec, all of France

[73] Assignee: Roussel Uclaf, Paris, France

[21] Appl. No.: 223,636

[22] Filed: Jul. 25, 1988

Related U.S. Application Data

[60] Division of Ser. No. 855,905, Apr. 24, 1986, Pat. No. 4,849,454, which is a division of Ser. No. 543,315, Oct. 19, 1983, Pat. No. 4,607,054, which is a continuation-in-part of Ser. No. 350,151, Feb. 19, 1982, Pat. No. 4,466,971.

[30] Foreign Application Priority Data

Feb. 23, 1981 [FR] France ................ 81 04630

[51] Int. Cl.$^5$ ............... C07C 49/403; C07C 49/497; C07C 49/603
[52] U.S. Cl. .................... 568/373; 560/256; 546/318
[58] Field of Search ............ 260/397.4; 568/373

[56] References Cited

U.S. PATENT DOCUMENTS

| | | | |
|---|---|---|---|
| 3,496,199 | 2/1970 | Uskokovic | 260/397 |
| 3,499,912 | 3/1970 | Uskokovic et al. | 549/279 |
| 3,956,316 | 5/1976 | Uskokovic et al. | 560/256 |

Primary Examiner—Alan L. Rotman

Attorney, Agent, or Firm—Bierman and Muserlian

[57] ABSTRACT

Novel antiandrogenic compositions comprising an antiandrogenically effective amount of at least one compound of the formula

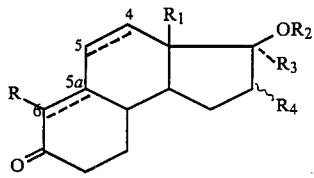

wherein R is alkyl of 1 to 4 carbon atoms, $R_1$ is alkyl of 1 to 2 carbon atoms, $R_2$ is selected from the group consisting of hydrogen, alkyl of 1 to 8 carbon atoms optionally interrupted with a heteroatom, alkenyl and alkynyl of 2 to 8 carbon atoms optionally interrupted with a heteroatom, formyl and acyl of an organic carboxylic acid of 2 to 18 carbon atoms, $R_3$ is selected from the group consisting of hydrogen, alkyl of 1 to 4 carbon atoms and alkenyl and alkynyl of 2 to 4 carbon atoms, $R_4$ is selected from the group consisting of hydrogen and alkyl of 1 to 4 carbon atoms, the dotted lines indicate optional presence of a double bond between the 4(5) and 5a(6) carbons and the wavy line indicates that $R_4$ may be in the α- or β-position and a non-toxic, pharmaceutical carrier or excipient and a method of treating hyperandrogenic conditions in warm-blooded animals.

5 Claims, No Drawings

PROCESS FOR PREPARING CERTAIN DECAHYDRO-7H-3-OL-7-ONES

This is a division of U.S. patent application Ser. No. 855,905 filed Apr. 24, 1986 U.S. Pat. No. 4,849,454 which is a division of Ser. No. 06/543,315, Oct. 19, 1983, U.S. Pat. No. 4,607,054, which is a continuation-in-part of Ser. No. 06/350,151, Feb. 19, 1982, U.S. Pat. No. 4,466,971.

STATE OF THE ART

Some of the compounds of formula I are known such as those described in Belgium Patent No. 663,197 and French Patent No. 1,359,675 and J. Org. Chem., 1969, Vol. 34(1), p. 107–112. Also pertinent is Swiss Patent No. 558,343 and European Patent Application Serial No. 0014,966 and U.S. Pat. Nos. 3,984,473 and 3,984,474.

OBJECTS OF THE INVENTION

It is an object of the invention to provide novel antiandrogenic compositions and a novel method of inducing antiandrogenic activity in warm-blooded animals.

It is another object of the invention to provide novel compounds of formula I' and a novel process for their preparation.

These and other objects and advantages of the invention will become obvious from the following detailed description.

THE INVENTION

The novel antiandrogenic compositions of the invention are comprised of

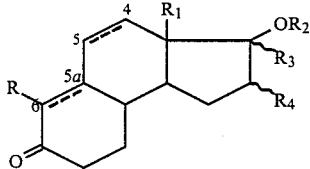

wherein R is alkyl of 1 to 4 carbon atoms, $R_1$ is alkyl of 1 to 2 carbon atoms, $R_2$ is selected from the group consisting of hydrogen, alkyl of 1 to 8 carbon atoms optionally interrupted with a heteroatom, alkenyl and alkynyl of 2 to 8 carbon atoms optionally interrupted with a heteroatom, formyl and acyl of an organic carboxylic acid of 2 to 18 carbon atoms, $R_3$ is selected from the group consisting of hydrogen, alkyl of 1 to 4 carbon atoms and alkenyl and alkynyl of 2 to 4 carbon atoms, $R_4$ is selected from the group consisting of hydrogen and alkyl of 1 to 4 carbon atoms, the dotted lines indicate optional presence of a double bond between the 4(5) and 5a(6) carbons and the wavy line indicates that $R_4$ may be in the $\alpha$- or $\beta$-position and a non-toxic pharmaceutical carrier. The compounds of formula I indicate products of natural series, racemic products and products of antipodal series.

Examples of R are methyl, ethyl, propyl, isopropyl, butyl, sec.-butyl, tert.-butyl and isobutyl. Examples of $R_2$ are alkyl such as methyl, ethyl, propyl, isopropyl, butyl, sec.-butyl, isobutyl, tert.-butyl, pentyl, sec-pentyl, iso-pentyl and linear or branched hexyl, heptyl and octyl, alkenyl such as vinyl, allyl and butenyl and alkynyl such as ethynyl, propynyl or butynyl.

When $R_2$ is alkyl, alkenyl or alkynyl interrupted by a heteroatom, $R_2$ preferably has the formula

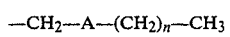

wherein A is oxygen or sulfur and n is a number from 0 to 4. $R_2$ in this instance is preferably methoxymethyl, lower alkoxymethyl such as ethoxymethyl or methylthiomethyl.

Examples of suitable organic carboxylic acids of 2 to 18 carbon atoms for the acyl of $R_2$ are optionally unsaturated aliphatic or cycloaliphatic carboxylic acids such as acetic acid, propionic acid, butyric acid, isobutyric acid, valeric acid, hexanoic acid, pivaloic acid, undecanoic acid, acrylic acid, crotonic acid, cyclobutyric acid, cyclopropane carboxylic acid and cyclopentyl carboxylic acid; cycloaklanoic acids such as cyclopentylacetic acid, cyclopentylpropionic acid, cyclohexylacetic acid and cyclohexylpropionic acid; benzoic acids; phenylalkanoic acids such as phenylacetic acid and phenylpropionic acid and hetero containing acids such as 3-pyridinyl-carboxylic acid, 4-pyridinyl-1-carboxylic acid, thiazolyl-carboxylic acid, 4,5-dihydrothiazolyl-carboxylic acid, oxazolyl-carboxylic acid and imidazolylcarboxylic acid and alkanoic acids interrrupted by a heteroatom such as methoxyacetic acid.

Examples of $R_3$ and $R_4$ as alkyl, alkenyl or alkynyl are the same groups discussed above for $R_2$.

Among the preferred compositions of the invention are those wherein R is methyl or ethyl, those wherein $R_3$ and $R_4$ are each hydrogen, those wherein the dotted line in the 4(5) position is not a double bond, those wherein the dotted line in the 5a(6) position is a double bond and those wherein $R_2$ is hydrogen, methoxymethyl, allyl, acetyl or butyryl. Specific preferred compounds are 3a$\beta$-methyl-6-ethyl-1,2,3,3a,4,5,8,9-,9a,9b-decahydro-7H-benz(e)inden-3$\beta$-ol-7-one, 3a$\beta$,6-diethyl-1,2,3,3a,4,5,8,9,9a,9b-decahydro-7H-benz(e)inden-3$\beta$-ol-7-one, 3a$\beta$-methyl-3$\beta$-acetoxy-6-ethyl-1,2,3,3a,4,5,8,9,9a,9b-decahydro-7H-benz(e)inden-7-one and 3$\beta$-(pyridin-3-yl)-carbonyloxy-3a$\beta$-methyl-6-ethyl-1,2,3,3a,4,5,8,9,9a,9b-decahydro-7H-benz(e)inden-7-one.

The compositions may be in the form of solutions, emulsions, creams, pomades, lotions, gelules, tablets, dragees, suppositories.

The compositions inhibit the effect of androgens on the level of peripherial organs without interfering with normal hypophysial functions. They may be used to treat adolescents without fear of arresting their growth and to treat adults without fear of certain effects of chemical castration.

The compositions may be used for treatment of local affections due to a hyperandrogenicity such as acne, hirsutism, seborrhea, hyperpilosity, androgen-dependent hair loss especially male pattern baldness (alopecia). The compositions may also be used as deodorants, particularly axillary deodorants. They may be in the usual form for topical application or rectal or oral administration.

Preferably the compositions are administered topically.

Examples of suitable excipients are aqueous or non-aqueous vehicles, lactose, starch, fatty bodies of animal or vegetable origin, paraffinic derivatives, glycols, diverse wetting agents, dispersants or emulsifiers and preservatives. When administered orally or rectally, the compositions are preferably gelules, tablets or suppositories.

When the compositions are applied topically, they are preferably in the form of an emulsion, cream, pomade or lotion containing 1 to 20%, preferably 2 to 10%, by weight of the compounds of formula I and it is applied 1 to 5 times per day.

The novel method of the invention for treating hyperandrogenocity in warm-blooded animals, including humans, comprises administering to warm-blooded animals an antiandrogenically effective amount of at least one compound of formula I. The usual daily dose will vary on the compound used, the condition treated and the method of administration.

The novel compounds of the invention have the formula

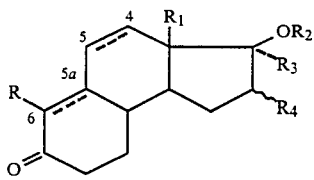

wherein R, $R_1$, $R_2$, $R_3$ and $R_4$, the dotted line and the wavy line have the above definition excluding the compounds wherein $R_4$ is hydrogen, the dotted line in the 4(5)-position is not a double bond and the dotted line in the 5a(6)-position is a double bond and (a) R is methyl, $R_3$ is hydrogen and (i) $R_2$ is hydrogen, acetyl, tert.-butyl or benzoyl and $R_1$ is methyl or (ii) $R_2$ is hydrogen or tert.-butyl and $R_1$ is ethyl, (b) R is ethyl or propyl, $R_3$ is hydrogen, $R_2$ is hydrogen or benzoyl and $R_1$ is methyl, (c) R is butyl, $R_1$ is methyl, $R_2$ is hydrogen and $R_3$ is hydrogen, (d) R is methyl, $R_1$ is methyl, $R_2$ is hydrogen and $R_3$ is methyl or ethyl and excluding the compound where-in $R_4$ is hydrogen and the dotted lines do not indicate a double bond and (a) $R_1$ and R are methyl, $R_3$ is hydrogen and $R_2$ is hydrogen, acetyl or benzoyl, (b) R and $R_1$ are methyl, $R_2$ is hydrogen and $R_3$ is ethyl, propargyl or isobutenyl, (c) $R_3$ is hydrogen and (i) R and $R_1$ are methyl and $R_2$ is methoxymethyl, (ii) R is ethyl, $R_1$ is methyl and $R_2$ is hydrogen or (iii) R is methyl, $R_1$ is ethyl and $R_2$ is hydrogen and (d) R, $R_1$ and $R_3$ are methyl and $R_2$ is hydrogen or acetyl.

The preferred compounds of formula I' are those where-in $R_4$ is alkyl of 1 to 4 carbon atoms, those wherein the dotted lines in the 4(5) and 5a(6)-positions are double bonds and those wherein the dotted line in the 5a(6)-position is a double bond and R and $R_1$ are ethyl. Specific preferred compounds of formula I' are 3aβ,6-diethyl-1,2,3,3a,4,5,8,9,9a,9b-decahydro-7H-benz(e)-inden-3β-ol-7-one, 3aβ-methyl-3β-acetoxy-6-ethyl-1,2,3,3a,4,5,8,9,9a,9b-decahydro-7H-benz(e)-inden-7-one and 3β-(pyridin-3-yl)-carbonyloxy-3aβ-methyl-6-ethyl-1,2,3,3a,4,5,8,9,9a,9b-decahydro-7H-benz(e)-inden-7-one.

The process of the invention for the preparation of compounds of the formula

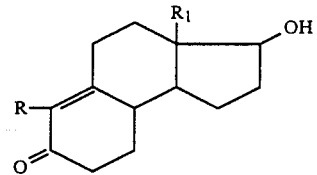

wherein R and $R_1$ have the above definitions with the proviso that R is not methyl, ethyl, n-propyl or n-butyl when $R_1$ is methyl and R is not methyl when $R_1$ is ethyl comprises reacting a compound of the formula

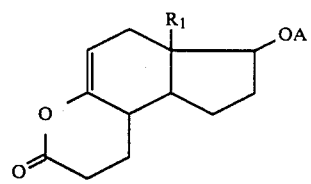

with a compound of the formula

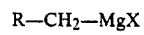

wherein A is acyl of an organic carboxylic acid of 2 to 18 carbon atoms and X is a halogen and saponifying the resulting ester to obtain a compound of formula $I_4'$.

The process for the preparation of a compound of the formula

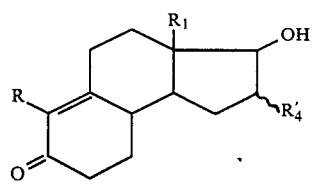

wherein R and $R_1$ have the above definition and $R_4'$ is alkyl of 1 to 4 carbon atoms comprises reacting a compound of the formula

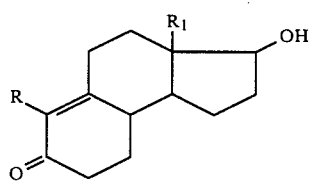

wherein R and $R_1$ have the above definition with a ketone protecting reactant to obtain a compound of the formula

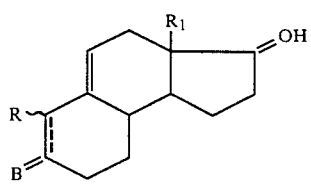

wherein B is a ketal, enamine or enol ether and the dotted line is a double bond when B is an enamine or enol ether, reacting the latter with an oxidation agent to obtain a compound of the formula

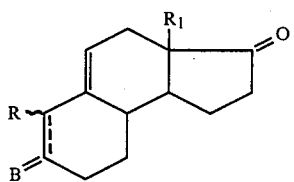   IV$_B$ treating the latter with an iodide of the formula R$_4'$ I in the presence of a strong base to form a compound of the formula

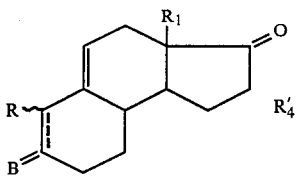   V$_B$ reacting the latter with a reducing agent to obtain a compound of the formula

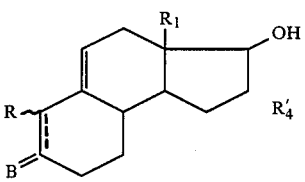   V$_B'$ and treating the latter to remove the ketone protecting group to obtain the compound of formula I$_B'$.

The novel process of the invention for the preparation of a compound of the formula

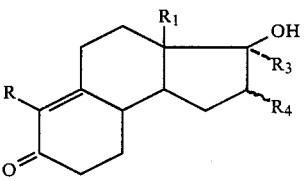   I$_C'$ wherein R, R$_1$, R$_3$ and R$_4$ have the above definition with the proviso that when R$_4$ is hydrogen, R and R$_1$ are not methyl when R$_3$ is ethyl comprises reacting a compound of the formula

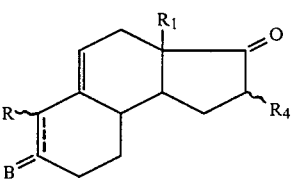   II$_C$ wherein B, R, R$_1$, R$_4$ and the dotted line have the above definition with a compound of the formula R$_3$-D wherein R$_3$ has the above definition and D is lithium or Mg-Hal and Hal is a halogen to obtain a compound of the formula

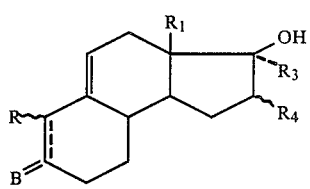   III$_C$ and treating the latter to remove the ketone protecting group to obtain the compound of formula I$_C'$.

The novel process of the invention for the preparation of a compound of the formula

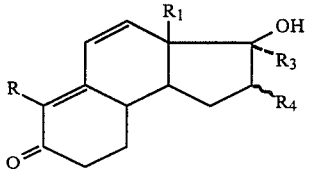   I$_D'$ wherein R, R$_1$, R$_3$ and R$_4$ have the above definitions comprises reacting a compound of the formula

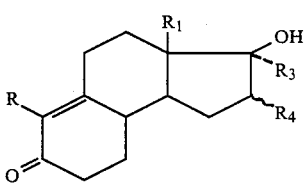   II$_D$ with a hydroxyl protecting reactant to obtain a compound of the formula

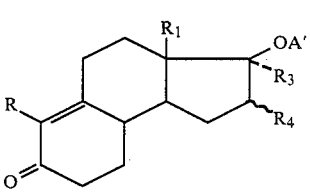   III$_D$ wherein A' is a hydroxyl protecting group, reacting the latter with a brominating agent to obtain a compound of the formula

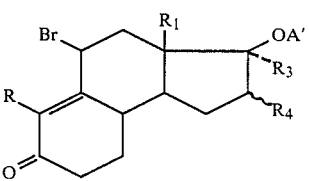   IV$_D$ and treating the latter with a dehydrobromination agent and an agent to remove the hydroxyl protecting group to obtain a compound of formula I$_D'$.

The novel process of the invention for the preparation of a compound of the formula

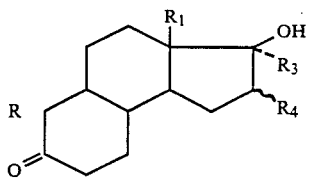

I'$_E$ wherein R, R$_1$, R$_3$ and R$_4$ have the above definition with the proviso that when R$_4$ is hydrogen, (a) R and R$_1$ are not methyl when R$_3$ is hydrogen, methyl, ethyl, propargyl or isobutenyl or (b) when R$_3$ is hydrogen, R is not methyl and R$_1$ is ethyl or R$_1$ is methyl and R is not ethyl comprises reacting a compound of the formula

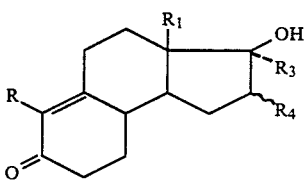

II'$_E$ with a hydrogenation agent to obtain the compound of formula I$_E$'.

The novel process of the invention for the preparation of a compound of the formula

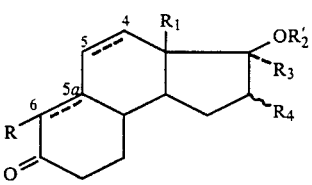

I'$_F$ wherein R, R$_1$, R$_3$, R$_4$ and the dotted lines have the above definitions and R$_2$' is R$_2$ other than hydrogen excluding the compounds wherein R$_4$ is hydrogen, the dotted line in the 4(5)-position is not a double bond and the dotted line in the 5a(6)-position is a double bond and (a) R is methyl, R$_3$ is hydrogen and (i) R$_2$' is acetyl, tert.-butyl or benzoyl and R$_1$ is methyl or (ii) R$_2$' is tert.-butyl and R$_1$ is ethyl, (b) R is ethyl or propyl, R$_3$ is hydrogen, R$_2$' is benzoyl and R$_1$ is methyl and excluding also the compounds wherein R$_4$ is hydrogen and the dotted lines do not indicate a double bond and (a) R$_1$ and R are methyl, R$_3$ is hydrogen and R$_2$' is acetyl or benzoyl, (b) R and R$_1$ are methyl, R$_2$' is methoxymethyl and R$_3$ is hydrogen and (c) R, R$_1$ and R$_3$ are methyl and R$_2$' is acetyl comprising either reacting a compound of the formula

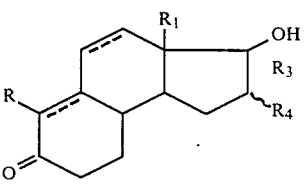

II$_F$ with a compound of the formula R$_2$'-E wherein E is a functional group residue and R$_2$' has the above definition to obtain the corresponding compound of formula I$_F$' or reacting a compound of the formula

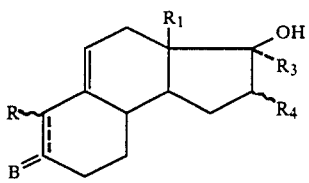

II'$_F$ wherein B has the above definition with a compound of the formula R$_2$'-E wherein R$_2$' and E have the above definition to obtain a compound of the formula

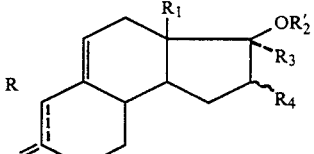

III'$_F$ and treating the latter to remove the ketone protecting group to obtain a compound of formula I$_F$' wherein there is no double bond in the 4(5)-position.

The condensation with the magnesium compound of formula III$_A$ which is preferably ethyl magnesium bromide is effected under the usual conditions for this type of reactant, preferably in an anhydrous organic solvent such as ethyl ether or tetrahydrofuran at low temperatures on the order of −50° C.

The saponification of the products is effected by treatment with a base such as sodium hydroxide, potassium hydroxide or baryta and the product may be recovered by treatment with an acid such as hydrochloric acid, acetic acid or sulfuric acid. In the compounds of formula II$_A$, A is preferably acetyl.

The 7-ketone protective groups of the compounds of formula III$_B$ are preferably ethylene ketal or pyrrolidine enamine and methoxy or ethoxy enol ethers. The ketone protective reactant for reaction with the compound of formula II$_B$ in this case would be ethylene glycol, pyrrolidine, methanol or ethanol. The reaction with ethylene glycol or monoalcohol is preferably effected in the presence of an acid such as p-toluene sulfonic acid.

The oxidation agent to react with the compound of formula III$_B$ is preferably pyridinium dichromate although other agents such as sulfochromic acid solution, pyridinium chlorochromate, chromium trioxide in pyridine or an Oppenhauer oxidation agent such as aluminum isopropoxide or aluminum tert.-butoxide may be used.

The strong base used in the presence of the reaction of the compound of formula IV$_B$ with R$_4$-I is preferably a lithium amide, especially lithium diisopropylamide formed in situ from butyllithium and diisopropylamine. Also useful are other strong bases such as alkali metal amides generally or alkali metal hydroxides such as sodium hydride. The reduction of the compounds of formula V$_B$ is preferably effected with lithium aluminum hydride although other hydrides such as sodium borohydride or potassium borohydride or lithium borohydride may be used.

The removal of the protective groups of formula V$_B$' may be effected by known means, especially by acid hydrolysis such as treatment with p-toluene sulfonic acid, hydrochloric acid or acetic acid.

The products of formulae $V_B$ and $V_B'$ may occur in the form of 2α-or 2β-isomers or in a form of a mixture of the said isomers which mixtures can be separated, if desired, by known methods such as chromatography. When only one of the isomers is obtained or is predominantly obtained, the other isomer can generally be obtained by isomerization of the obtained sole isomer. The isomerization may be effected by heating in a basic medium such as a potassium methanolate solution and the resulting mixture may be separated by known methods such as chromatography. The isomerization or isomer separation is preferably effected with the compounds of formula $V_B$.

The magnesium derivative for reaction with a compound of formula $II_C$ is preferably an alkyl magnesium bromide in an organic solvent such as tetrahydrofuran or ether. The removal of the ketone protecting group is effected as discussed above.

The hydroxyl protection of the compounds of formula $II_D$ may be effected in a known manner preferably by esterification as the acetyl group by reaction with acetic anhydride but equally useful is protection with a tetrahydropyranyl group. The formation of the 4(5)-double bond is preferably effected with N-bromosuccinimide followed by treatment with a dehydrobromination agent such as pyridine, collidine or a mixture of lithium carbonate and lithium bromide.

The removal of the hydroxyl group is effected by known methods. When the protection is effected by ester such as acetyl, the group is removed by the saponification conditions described above. When the hydroxyl group is protected by tetrahydropyranyl, it is removed by acid hydrolysis under the usual conditions. The hydrogenation of the compounds of formula $II_E'$ is effected, for example, with hydrogen in the presence of a catalyst such as platinum or platinum oxide.

The reactant, $R_2'$-E, which is reacted with a compound of formulae $II_F$ or $II_F'$ is a halide of alkyl alkenyl or alkynyl optionally interrupted with a heteroatom. The halide is preferably chloride or bromide and the reaction is effected in the presence of an organic base such as triethylamine or a mineral base or basic salt such as sodium bicarbonate, lithium bicarbonate or potassium bicarbonate.

The hydroxyl group may also be esterified by reaction with a mixed or symmetrical anhydride such as acetic anhydride or butyric anhydride or with an acyl halide such as acetyl chloride. The removal of the protective group of formula $III_F'$ is effected as discussed above.

The preparation of the racemic products and the antipodal compounds is effected in the same fashion beginning from the corresponding starting materials.

The starting compounds of formula $II_A$ may be prepared by the processes of French Patent No. 1,364,556 and No. 1,476,509. The starting products of formula $II_B$ are partially a part of the compounds of formula $I_A'$ and may be prepared by the process of the application and the other compounds are described in J. Org. Soc., 1962, p. 1312–1313; Helv. Chim. Acta. Vol. 54(7) (1971), p. 2121–2132; J. Org. Chem., Vol. 34(1) (1969), p. 107–112; French Patent No. 1,359,675.

The starting compounds of formula $II_C$ are partially within the scope of formula $V_B$ and may be prepared by the described process and the compounds wherein $R_4$ is hydrogen are described in French Patent No. 1,553,958. The starting compounds of formula $II_D$ are partially within formula $I_C'$ and may be prepared accordingly and the other compounds are known in Belgium Patent No. 663,197. The compounds of formula $II_E'$ are within the scope of formula $II_D$.

The starting products of formula $II_F$ are described above and the starting products of formula $II_{F'}$ are prepared in an analogous manner to that for the compounds of formula $III_B$ described above. The same process may be used for the starting compounds of formula $II_F$ with a double bond lacking in the 4(5)-position.

The compounds of formula I which are not within the scope of formula I' which may be prepared by the process of the invention are known. They may be prepared by the processes mentioned herein after.

The compounds of formula I with a double bond in the 5a(6)-position and wherein R is methyl and $R_3$ is hydrogen may be prepared by the processes of French Patent No. 1,359,675, J. Org. Chem., Vol. 34(5) (1969), p. 1457–1458; Ann. Vol. 669 (1963), p. 153–159; J. Org. Chem., Vol. 34(1) (1969), p. 107–112 and German Application OLS 1,811,693. The compounds of formula I with a double bond in the 5a(6)-position and wherein $R_3$ is hydrogen and R is alkyl other than methyl may be prepared by the process of French Patent No. 1,359,675 and Helv. Chim. Acta., Vol. 54(7) (1971), p. 2121–2132.

The compounds of formula I having a double bond in the 5a(6)-position and $R_3$ is other than hydrogen may be prepared by the process of Belgium Patent No. 663,197. The compounds of formula I with no unsaturation and with $R_3$ being hydrogen and $R_1$ being methyl may be prepared by the processes described in Belgium Patent No. 663,197, U.S. Pat. Nos. 3,956,316 and 3,644,429 and J. Chem. Soc. 1949, p. 1855–1865 and J. Chem. Soc., 1962, p. 1312–1313.

The saturated products of formula I wherein $R_3$ is hydrogen and $R_1$ is ethyl may be prepared as described in Belgium Patent No. 767,347 and the saturated products wherein $R_1$ is methyl and $R_3$ is other than hydrogen may be prepared by Belgium Patent No. 663,197 and U.S. Pat. No. 3,496,199.

In the Examples, the nomenclature used is derived from the following numbering system.

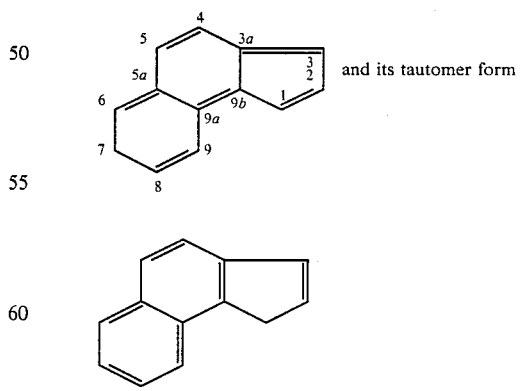

and its tautomer form

In the following examples there are described several preferred embodiments to illustrate the invention. However, it should be understood that the invention is not intended to be limited to the specific embodiments.

EXAMPLE 1

2α,3aβ,6-trimethyl-1,2,3,3a,4,5,8,9,9a,9b-decahydro-7H-benz(e)-inden-3β-ol-7-one STEP A: 3a, 6-dimethyl-7,7-ethylenedioxy-1,2,3,3a,4,6,8,9,9a,9b-decahydro-7H-benz(e)-inden-3β-ol A mixture of 5.5 g of 3a, 6-dimethyl-1,2,3,3a,4,5,8,9,-,9a,9b-decahydro-7H-benz(e)-inden-3β-ol-7-one, 5.5 ml of ethylene glycol, 9 ml of ethyl orthoformate, 200 mg of p-toluene sulfonic acid and 200 ml of benzene was refluxed under nitrogen for 3 hours and anhydrous sodium carbonate was added thereto. The mixture was washed with sodium hydroxide solution and was evaporated to dryness. The residue was chromatographed over silica gel and eluted with a 1-9 acetone-hexane mixture to obtain 3.22 g of 3a, 6-dimethyl-7,7-ethylenedioxy-1,2,3,3a,4,6,8,9,9a,9b-decahydro-7H-benz(e)-inden-3β-ol.

STEP B: 3aβ,6-dimethyl-7,7-ethylenedioxy-1,2,3,3a,4,6,8,9,9a,9b-decahydro-7H-benz(e)-inden-3-one 1.9 g of the product of Step A were oxidized with 6.37 g of pyridinium dichromate in 19.5 ml of a dimethylformamide-methylene chloride mixture at room temperature for 2 hours. The product was taken up in water and the aqueous phase was extracted with ether. The organic phase was evaporated to dryness and the residue was crystallized from hexane to obtain 1.235 g of an epimeric mixture of 3aβ,6-dimethyl-7,7-ethylenedioxy-1,2,3,3a,4,6,8,9,9a,9b-decahydro-7H-benz(e)-inden-3-one melting at 95° C.

NMR Spectrum (deuterochloroform):
Peak at 0.85 ppm (methyl at 3a)

STEP C: 2α,3aβ,6-trimethyl-7,7-ethylenedioxy-1,2,3,3a,4,6,8,9,9a,9b-decahydro-7H-benz(e)-inden-3-one A solution was prepared under a nitrogen atmosphere at 0° C. of 0.17 ml of diisopropylamine and a hexane solution of 1.6M of butyllithium in 2 ml of tetrahydrofuran in the presence of a bipyrydil crystal as a color indicator and after 10 minutes, the red solution was admixed at 0° C. with a mixture of 276 mg of the product of Step B and 1 ml of tetrahydrofuran. The temperature was allowed to rise to room temperature and after 20 minutes, 0.4 ml of methyl iodide was added to the mixture. The color of the mixture turned yellow and a precipitate rapidly appeared. The mixture was poured into water and was extracted with ether to obtain 294 mg of a product melting at 110° C. The latter was crystallized from a hexane-ether mixture to obtain 225 mg of 2α,3aβ,6-trimethyl-7,7-ethylenedioxy-1,2,3,3a,4,6,8,9,-,9a,9b-decahydro-7H-benz(e)-inden-3-one melting at 136° C.

NMR Spectrum (deuterochloroform):
Peak at 0.87 ppm (3a-methyl).

STEP D: 2α,3aβ,6-trimethyl-7,7-ethylenedioxy-1,2,3,3a,4,6,8,9,9a,9b-decahydro-7H-benz(e)-inden-3β-ol 130 mg of the product of Step C were reacted with 32 mg of lithium aluminum hydride in ether at room temperature for 10 minutes and the mixture was hydrolyzed with water and 15% sodium hydroxide. The mixture was filtered and the filtrate was evaporated to dryness to obtain an oil of 2α,3aβ,6-trimethyl-7,7ethylenedioxy-1,2,3,3a,4,6,8,9,9a,9b-decahydro-7H-benz(e)-inden-3β-ol.

NMR Spectrum (deuterochloroform):
Peaks at 0.72 ppm (3a methyl)

STEP E: 2α,3aβ,6-trimethyl-1,2,3,3a,4,5,8,9,9a,9b-decahydro-7H-benz(e)-inden-3β-ol-7-one A mixture of the product of Step D in aqueous acetone in the presence of a few mg of p-toluene sulfonic acid was heated to reflux and cooled. The mixture was extracted with ether and the extract was chromatographed over silica gel. Elution with an 8-2 acetone-hexane mixture and crystallization of the product from aqueous methanol yielded 60 mg of 2α,3aβ,6-trimethyl-1,2,3,3a,4,5,8,9,9a,9b-decahydro-7H-benz(e)-inden-3β-ol-7-one melting at 139° C. and having a specific rotation of $[\alpha]_D^{25} = -51°$ (c=1% in chloroform).

NMR Spectrum (deuterochloroform):
Peak at 0.90 ppm (3a methyl)

Analysis: $C_{16}H_{24}O_2$: Calculated: % C 77.37,% H 9.74; Found: % C 77.1,% H 9.6.

EXAMPLE 2

2β,3aβ,6-trimethyl-1,2,3,3a,4,5,8,9,9a,9b-decahydro-7H-benz(e)-inden-3β-ol-7-one STEP A: 2β,3aβ,6-trimethyl-7,7-ethylenedioxy-1,2,3,3a,4,6,8,9,9a,9b-decahydro-7H-benz(e)-inden-3-one A mixture of 240 mg of the product of Step C of Example 1 in 2.6 ml 2N potassium methanolate was refluxed for 90 minutes and was evaporated to dryness. The residue was taken up in water and the aqueous phase was extracted with ether to obtain a 1-1 mixture of 2α and 2β-isomers of the desired compound. The mixture was chromatographed over silica gel and was eluted with a 1-9 ethyl acetate-hexane mixture to obtain 110 mg of 2β,3aβ,6-trimethyl-7,7-ethylenedioxy-1,2,3,3a,4,6,8,9,9a,9b-decahydro-7H-benz(e)-inden-3-one in the form of an oil.

NMR Spectrum (deuterochloroform):
Peak at 0.8 ppm (3a methyl)

STEP B: 2β,3aβ,6-trimethyl-1,2,3,3a,4,5,8,9,9a,9b-decahydro-7H-benz(e)-inden-3β-ol-7-one Using the product of Step D of Example 1, the 110 mg of the product of Step A were reacted to obtain 2β,3aβ,6-trimethyl-7,7-ethylenedioxy-1,2,3,3a,4,6,8,9,-,9a,9b-decahydro-7H-benz(e)-inden-3β-ol which was reacted as in Step E of exemple 1 to obtain 70 mg of 2β,3aβ,6-trimethyl-1,2,3,3a,4,5,8,9,9a,9b-decahydro-7-H-benz(e)-inden-3β-ol-7-one which melted at 81° C. after crystallization from an ether-hexane mixture. The product had a specific rotation of $[\alpha]_D^{25} = -32°$ (c=1% in chloroform).

Analysis: $C_{16}H_{24}O_2$: Calculated: % C 77.37,% H 9.74, Found: % C 77.2,% H 9.8.

EXAMPLE 3

3aβ,6-diethyl-1,2,3,3a,4,5,8,9,9a,9b-decahydro-7H-benz(e)-inden-3β-ol-7-one 3.36 ml of an 0.8M of freshly prepared n-propyl magnesium bromide in ether were added slowly at −60° C. to a solution of 500 mg of the δ lactone of 1β-acetoxy-4-(2'-carboxyethyl)-5-hydroxy-7a-ethyl-3a,4β,7,7a-tetrahydro-indane in 3.8 ml of anhydrous tetrahydrofuran and after one hour of reaction at −60° C., excess magnesium was destroyed by addition of water. The tetrahydrofuran was evaporated and an aqueous saturated ammonium chloride solution was added to the mixture. The mixture was extracted with ether and the ether phase was dried and evaporated to dryness. The residue was adminxed with 3.7 ml of 2N potassium methanolate and the mixture was refluxed for one hour and was neutralized with acetic acid. The mixture was evaporated to dryness and the residue was taken up in water. The aqueous phase was extracted with methylene chloride and the organic phase was evaporated to dryness to obtain 470 mg of raw product. The latter was crystallized from an acetone-hexane mixture to obtain 100 mg of 3a$\beta$,6-diethyl-1,2,3,3a,4,5,8,9,9a,9b-decahydro-7H-benz(e)-inden-3$\beta$-ol-7-one melting at 131.5° C. and having a specific rotation of $[\alpha]_D^{25} = -58°$ (c=1% in methanol).

Analysis: $C_{17}H_{26}O_2$: Calculated: % C 77.82,% H 9.99, Found: % C 78.0,% H 10.0.

EXAMPLE 4

3a$\beta$-ethyl-6-propyl-1,2,3,3a,4,5,8,9,9a,9b-decahydro-7H-benz(e)-inden-3$\beta$-ol-7-one Using the procedure of Example 3, 500 mg of δ lactone of 1$\beta$-acetoxy-4-(2'-carboxyethyl)-5-hydroxy-7a-ethyl-3a,4$\beta$,7,7a-tetrahydroindane and n-butyl magnesium bromide were reacted to obtain 220 mg of residue which was crystallized from acetone to obtain 105 mg of 3a$\beta$-ethyl-6-propyl-1,2,3,3a,4,5,8,9,9a,9b-decahydro-7H-benz(e)-inden-3$\beta$-ol-7-one melting at 127° C. and having a specific rotation of $[\alpha]_D^{25} = -55°$ (c=1% in methanol).

Analysis: $C_{18}H_{28}O_2$: Calculated: % C 78.21,% H 10.21, Found: % C 78.4,% H 10.1.

EXAMPLE 5

3a$\beta$,ethyl-6-methyl-3$\beta$-acetoxy-1,2,3,3a,4,5,8,9,9a,9b-decahydro-7H-benz(e)-inden-7-one Acetic anhydride and a solution of 3a$\beta$-ethyl-6-methyl-1,2,3,3a,4,5,8,9,9a,9b-decahydro-7H-benz(e)-inden-3$\beta$-ol-7-one in pyridine were reacted and the resulting product was crystallized from aqueous methanol to obtain 3a$\beta$,ethyl-6-methyl-3$\beta$-acetoxy-1,2,3,3a,4,5,8,9,9a,9b-decahydro-7H-benz(e)-inden-7-one melting at 99° C.

EXAMPLE 6

3a$\beta$-ethyl-6-methyl-1,2,3,3a,8,9,9a,9b-octahydro-7H-benz(e)-inden-3$\beta$-ol-7-one STEP A: 3a$\beta$-ethyl-5-bromo-6-methyl-3$\beta$-acetoxy-1,2,3,3a,4,5,8,9,9a,9b-decahydro-7H-benz(e)-inden-7-one A mixture of 210 mg of the product of Example 5, 0.72 ml of acetic anhydride and 10 mg of p-toluenesulfonic acid stood for 16 hours and then 0.3 ml of acetic acid and 0.43 ml of water were added thereto. The mixture stood at room temperature for 2 hours and was then cooled to 5° C. and mixed with 130 mg of N-bromosuccinimide. The mixture was stirred for 2 hours and 0.72 ml of water were added thereto. The mixture was filtered to obtain 190 mg of 3a$\beta$-ethyl-5-bromo-6-methyl-3$\beta$-acetoxy-1,2,3,3a,4,5,8,9,9a,9b-decahydro-7H-benz(e)-inden-7-one melting at ≃120° C.

STEP B: 3a$\beta$-ethyl-6-methyl-1,2,3,3a,8,9,9a,9b-octahydro-7H-benz(e)-inden-3$\beta$-ol-7-one A mixture of 190 mg of the product of Step A, 95 mg of lithium bromide and 47 mg of lithium carbonate in 4.5 ml of dimethylformamide was distilled for 30 minutes under nitrogen almost to dryness and was then cooled. 5 ml of water and 0.1 ml of acetic acid were added to the mixture and the mixture was poured into water. The mixture was extracted with methylene chloride and the organic phase was evaporated to dryness to obtain 128 mg of product. The latter was chromatographed over silica gel and was eluted with an acetone-hexane mixture to obtain 3a$\beta$-ethyl-6-methyl-1,2,3,3a,8,9,9a,9b-octahydro-7H-benz(e)-inden-3$\beta$-ol-7-one melting at 155° C. and having a specific rotation of $[\alpha]_D^{25} = -207°$ (c=1% in chloroform).

Analysis: $C_{16}H_{22}O_2.0.5$:

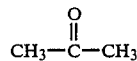

Calculated: % C 76.32,% H 9.15, Found: % C 76.65,% H 9.3.

EXAMPLE 7

Butanoate of 3a$\beta$-methyl-6-ethyl-7-oxo-1,2,3,3a,4,5,8,9,9a,9b-decahydro-1H-benz(e)-inden-3-yl 30 mg of 4-dimethylamino-pyridine were added to a solution of 0.75 g of 3a$\beta$-methyl-6-ethyl-1,2,3,3a,4,5,8,9,9a,9b-decahydro-7H-benz(e)-inden-3$\beta$-ol-7-one, 1.5 ml of butyric acid anhydride and 1.05 ml of dry triethylamine and the mixture was stirred at room temperature for 2 hours and was poured into aqueous saturated sodium bicarbonate solution. The mixture was stirred for 2 hours and was extracted with methylene chloride. The organic phase was washed with water, dried and evaporated to dryness to obtain 0.96 g of an oil. The latter was chromatographed over silica gel and was eluted with a 9-1 benzene-ethyl acetate mixture to obtain butanoate of 3a$\beta$-methyl-6-ethyl-7-oxo-1,2,3,3a,4,5,8,9,9a,9b-decahydro-1H-benz(e)-inden-3-yl.

Analysis: $C_{20}H_{30}O_3$: Calculated: % C 75.43,% H 9.49, Found: % C 75.6,% H 9.50.

NMR Spectrum (deuterochloroform):

Peaks at 0.9 ppm (t) (hydrogens of methyl of $CH_3-CH_2-$); at 0.97 ppm (hydrogens of 3a methyl); at 0.97 ppm (t) (hydrogens of methyl of $CH_3-CH_2-$); at 4.68 ppm (t) (3$\alpha$-hydrogen) (J=8 Hz).

EXAMPLE 8

3-methoxy-methoxy-3a$\beta$-methyl-6-ethyl-1,2,3,3a,4,5,8,9,9a,9b-decahydro-7H-benz(e)-inden-7-one 1 g of lithium carbonate and 1 ml of methoxymethyl chloride were added at room temperature to a solution of 2 g of 3a$\beta$-methyl-6-ethyl-1,2,3,3a,4,5,8,9,9a,9b-decahydro-7H-benz(e)-inden-3$\beta$-ol-7-one in 20 ml of dry dimethylformamide and then 1 g of lithium carbonate and 1 ml of methoxymethyl chloride were successively added 2,4 and 5 hours later. Another 1 ml of methoxymethyl chloride was added to the mixture at the 6th hour and one hour later, the mixture was poured into a mixture of 40 ml of aqueous saturated sodium bicarbonate solution and 80 ml of water. The mixture was extracted with ethyl acetate and the organic phase was washed with water, dried and evaporated to dryness. The 2.4 of oil residue were chromatographed over silica gel and eluted with a 7-3 benzene-ethyl acetate mixture to obtain 1.6 g of 3-methoxy-methoxy-3a$\beta$-methyl-6-ethyl-1,2,3,3a,4,5,8,9,9a,9b-decahydro-7H-benz(e)-inden-7-one with an Rf=0.48.

Analysis: $C_{18}H_{28}O_3$: Calculated: % C 73.93,% H 9.65, Found: % C 73.9,% H 9.7.

NMR Spectrum (deuterochloroform):

Peaks at 0.9 ppm (t) (hydrogens of methyl of 6—CH$_3$—CH$_2$); at 0.96 ppm (hydrogens of 3a-methyl); at 3.58 ppm (t) (3-hydrogen); at 4.06 ppm (hydrogens of CH$_3$—O); at 4.68 ppm (hydrogens of methylene of CH$_3$—O—CH$_2$—)

EXAMPLE 9

3aβ-methyl-3-(2-propenyloxy)-6-ethyl-1,2,3,3a,4,5,8,9,9a,9b-decahydro-7H-benz(e)-inden-7-one STEP A: 1,2,3,3a,4,6,8,9,9a,9b-decahydro-6β-ethyl-3aβ-methylspiro-[7H-benz(e)-indene-7,2'-(1,3)-dioxolane]-3β-ol A suspension of 4 g of 3a-methyl-6β-ethyl-1,2,3,3a,4,5,8,9,9a,9b-decahydro-7H-benz(e)-inden-3β-ol-7-one, 40 ml of ethyleneglycol and 4 ml of ethyl orthoformate was heated to 75° C. and 20 mg of p-toluene sulfonic acid were added thereto all at once. The mixture was stirred for 3 hours and another 20 mg of p-toluene sulfonic acid were added. The mixture was heated at 75° C. for one hour and was then cooled. 1 ml of triethylamine was added to the mixture which was then poured into 80 ml of water. The mixture was extracted with ethyl acetate and the organic phase was washed with water, dried and evaporated to dryness. The 4.6 g of resin residue were chromatographed over silica gel and eluted with a 1-1 cyclohexane-ethyl acetate mixture to obtain 3.4 g of 1,2,3,3a,4,6,8,9,9a,9b-decahydro-6β-ethyl-3aβ-methyl-spiro-[7H-benz(e)-indene-7,2'-(1,3)-dioxolane]-3β-ol melting at 148° C.

STEP B: 3aβ-methyl-3-(2-propenyloxy)-6β-ethyl-1,2,3,3a,4,6,8,9,9a,9b-decahydro-7,7-ethylenedioxy-7H-benz(e)-indene 0.489 g of a 50% suspension of sodium hydride in oil were added to a solution of 3 g of the product of Step A in 30 ml of tetrahydrofuran and the mixture was held in an oil bath at 45° C. 3 ml of allyl bromide were added to the mixture which was heated for 3 hours at 45° C. after which another 3 ml of allyl bromide were added. The mixture was heated for another 3 hours at 45° C. and was refluxed for one hour and cooled. The mixture was poured into 300 ml of aqueous saturated sodium bicarbonate solution and the mixture was extracted with ethyl acetate. The organic phase was washed with water, dried and evaporated to dryness to obtain 3.5 g of an oil residue. 250 mg of the product were chromatographed over silica gel and eluted with a 7-3 benzene-ethyl acetate mixture to obtain 0.16 g of 3aβ-methyl-3-(2-propenyloxy)-6β-ethyl-1,2,3,3a,4,6,8,9,9a,9b-decahydro-7,7-ethylenedioxy-7H-benz(e)-indene.

NMR Spectrum (deuterochloroform):

Peaks at 0.76 ppm (hydrogens of 3a-methyl); at 0.81 ppm (t) (hydrogens of terminal CH$_3$ of 6-ethyl) (J=7 Hz); at 3.5 ppm (3α-hydrogen); at 4 ppm (m) (hydrogens of —O—CH$_2$—CH=CH$_2$); at 5.66 ppm (m) (hydrogen of —O—CH$_2$—CH=CH$_2$).

STEP C: 3aβ-methyl-3-(2-propenyloxy)-6-ethyl-1,2,3,3a,4,5,8,9,9a,9b-decahydro-7H-benz(e)-inden-7-one A solution of 3 g of the product of Step B, 18 ml of 2N aqueous hydrochloric acid and 450 ml of methanol was stirred at room temperature for 4 hours and the methanol was evaporated. The residue was taken up in 45 ml of water and the mixture was extracted with ethyl acetate. The organic phase was washed with aqueous sodium bicarbonate solution, with water, dried and evaporated to dryness. The 2.5 g of oil residue were chromatographed over silica gel and eluted with a 7-3 benzene-ethyl acetate mixture to obtain 1.64 g of 3aβ-methyl-3-(2-propenyloxy)-6-ethyl-1,2,3,3a,4,5,8,9,9a,9b-decahydro-7H-benz(e)-inden-7-one.

Analysis: C$_{19}$H$_{28}$O$_2$: Calculated: % C 79.12, % H 9.78, Found: C 79.3, H 9.9.

NMR Spectrum (deuterochloroform):

Peaks at 0.91 ppm (t) (hydrogens of terminal CH$_3$ at 6) (J=7 Hz); at 0.96 ppm (hydrogens of 3a methyl); at 3.43 ppm (t) (3α-hydrogen); at 5.26 ppm (m) (hydrogens of methylene of —CH=CH$_2$); at 5.98 ppm (m) (hydrogen of —CH=CH$_2$).

EXAMPLE 10

3aβ-methyl-3β-acetoxy-6-propyl-1,2,3,3a,4,5,8,9,9a,9b-decahydro-7H-benz(e)-inden-7-one 9.6 ml of an ether solution of 0.8M of freshly prepared n-butyl magnesium bromide were added at −60° C. over 30 minutes to a solution of 1.35 g of the γ-lactone of 1β-acetoxy-4-(2'-carboxyethyl)-5-hydroxy-7aβ-methyl-3aα,4β,7,7a-tetrahydro-indane in 10 ml of anhydrous tetrahydrofuran and after stirring at −60° C. for one hour, 15 ml of water were added thereto to destroy excess magnesium reactant. The mixture was evaporated to dryness and the residue was added to aqueous saturated ammonium chloride solution. The mixture was extracted with ether and the organic phase was dried and evaporated to dryness to obtain 1.43 g of 3aβ-methyl-3β-acetoxy-6-propyl-1,2,3,3a,4,5,8,9,9a,9b-decahydro-7H-benz(e)-inden-7-one.

EXAMPLE 11

3aβ,6-dimethyl-3β-acetoxy-1,2,3,3a,8,9,9a,9b-octahydro-7H-benz(e)-inden-7-one

STEP A: 3aβ,6-dimethyl-5-bromo-3β-acetoxy-1,2,3,3a,4,5,8,9,9a,9b-decahydro-7H-benz(e)-inden-7-one A mixture of 23.4 g of 3aβ,6-dimethyl-1,2,3,3a,4,5,8,9,9a,9b-decahydro-7H-benz(e)-inden-3β-ol-7-one, 100 ml of acetic anhydride and 1 g of p-toluene sulfonic acid was stirred and then allowed to stand at about 20° C. for 16 hours. 40 ml of acetic acid and 60 ml of water were added to the mixture at less than 30° C. and was then held at 5° C. for 2 hours. 17.8 g of N-bromo-succinimide were added to the mixture over 10 minutes while keeping the temperature below 15° C. and the mixture was stirred for 30 minutes and poured into 100 ml of water. The mixture was vacuum filtered and the product was washed with ethanol containing 40% of water then with ethanol and dried at 40° C. to obtain 26.3 g of 3aβ,6-dimethyl-5-bromo-3β-acetoxy-1,2,3,3a,4,5,8,9,9a,9b-decahydro-7H-benz(e)-inden-7-one which after crystallization from a methylene chloride-isopropyl ether mixture melted at 140° C. and had a specific rotation of [α]$_D^{25}$= +226°±3° (c=1% in chloroform).

Analysis: C$_{17}$H$_{23}$O$_3$Br: Calculated: % C 57.47, % H 6.52, Found: C 57.8, H 6.7.

STEP B: 3aβ,6-dimethyl-3β-acetoxy-1,2,3,3a,8,9,9a,9b-octahydro-7H-benz(e)-inden-7-one A mixture of 2 g of lithium bromide, 1 g of lithium carbonate and 90 ml of dimethylformamide was distilled to remove 10 ml for drying and 4 g of the product of Step A were added thereto. The mixture was evaporated to about 50 ml in 30 minutes and was cooled and 100 ml of water and then 2 ml of acetic acid were added to the mixture which was poured into water. The mixture was extracted 3 times with methylene chloride and the combined organic phases were washed with water, dried and evaporated to dryness. The residue was chromatographed over silica gel and eluted with 95-5 methylene chloride-isopropyl ether mixture. The product was crystallized from petroleum ether to obtain 2.32 g of 3aβ,6-dimethyl-3β-acetoxy-1,2,3,3a,8,9,9a,9b-octahydro-7H-benz(e)-inden-7-one melting at 75° C. and having a specific rotation of $[\alpha]_D^{25} = -143° \pm 1.5°$ (c=1% in chloroform).

Analysis: $C_{17}H_{22}O_3$: Calculated: % C 74.42, % H 8.08, Found: C 74.5, H 8.2.

EXAMPLE 12

3aβ,6-dimethyl-1,2,3,3a,8,9,9a,9b-octahydro-7H-benz(e)-inden-3β-ol-7-one

A mixture of 15.2 g of the product of Example 11, 152 ml of ethanol and 55 ml of 2N sodium hydroxide solution stood at 20° C. for 2 hours and then 600 ml of water were slowly added thereto. The mixture was vacuum filtered and the product was washed with water and dried to obtain 11.6 g of product. The latter was dissolved in methylene chloride and the solution was treated with activated carbon and isopropyl ether was added. The mixture was concentrated under reduced pressure at about 30° C. and was vacuum filtered. The product was washed with isopropyl ether and dried to obtain 11.3 g of 3aβ,6-dimethyl-1,2,3,3a,8,9,9a,9b-octahydro-7H-benz(e)-inden-3β-ol-7-one melting at 156° C. and having a specific rotation of $[\alpha]_D^{25} = -188° \pm 2°$ (c=1% in chloroform).

Analysis: $C_{15}H_{20}O_2$: Calculated: % C 77.55, % H 8.68, Found: C 77.5, H 8.7.

EXAMPLE 13

3β-acetoxy-3aβ-methyl-6-ethyl-1,2,3,3a,4,5,8,9,9a,9b-decahydro-7H-benz(e)-inden-7-one 12 ml of pure acetic anhydride were rapidly added to a solution of 6 g of 3aβ-methyl-6-ethyl-1,2,3,3a,4,5,8,9,,9a,9b-decahydro-7H-benz(e)-inden-3β-ol-7-one in 24 ml of pyridine and the solution was held at room temperature for 15 hours. The mixture was poured into 240 ml of water and the mixture was filtered. The product was washed with water and dried to obtain 6.8 g of product which was crystallized from hexane to obtain 6.5 g of 3β-acetoxy-3aβ-methyl-6-ethyl-1,2,3,3a,4,5,8,9,,9a,9b-decahydro-7H-benz(e)-inden-7-one melting at 90° C.

Analysis: $C_{18}H_{26}O_3$: Calculated: % C 74.44, % H 9.02, Found: C 74.4, H 9.1.

NMR Spectrum (deuterochloroform):

Peaks at 0.91 ppm (t) (hydrogens of $CH_3$ of 6-ethyl) (J=8 Hz); at 0.97 ppm (hydrogens of 3a-methyl); at 2.06 ppm (hydrogens of acetoxy); at 4.65 ppm (t) (3α-hydrogen) (J=8 Hz).

EXAMPLE 14

3aβ-methyl-3β-propionyloxy-6-ethyl-1,2,3,3a,4,5,8,9-,9a,9b-decahydro-7H-benz(e)-inden-7-one Using the procedure of Example 13, 1 g of 3aβ-methyl-6-ethyl-1,2,3,3a,4,5,8,9,9a,9b-decahydro-7H-benz(e)-inden-3β-ol-7-one and 2 ml of propionic anhydride were reacted and the product was extracted with ether. The organic phase was washed with aqueous saturated sodium bicarbonate solution, with water, dried and evaporated to dryness. The residue was chromatographed over silica gel and was eluted with a 9-1 benzene-ethyl acetate mixture to obtain 1.08 g of 3aβ-methyl-3β-propionyloxy-6-ethyl-1,2,3,3a,4,5,8,9,9a,9b-decahydro-7H-benz(e)-inden-7-one melting at 50° C. and having a specific rotation of $[\alpha]_D^{25} = -28° \pm 2°$ (c=0.4% in ethanol).

Analysis: $C_{19}H_{28}O_3$: Calculated: % C 74.96, % H 9.27, Found: C 75.0, H 9.2.

EXAMPLE 15

3aβ-methyl-3β-valeryloxy-6-ethyl-1,2,3,3a,4,5,8,9-,9a,9b-decahydro-7H-benz(e)-inden-7-one Using the procedure of Example 14, 0.5 g of 3aβ-methyl-6-ethyl-1,2,3,3a,4,5,8,9,9a,9b-decahydro-7-H-benz(e)-inden-3β-ol-7-one and 1 ml of valeryl anhydride were reacted to obtain 0.590 g of 3aβ-methyl-3β-valeryloxy-6-ethyl-1,2,3,3a,4,5,8,9,9a,9b-decahydro-7H-benz(e)-inden-7-one with a specific rotation of $[\alpha]_D^{25} = -18° \pm 2°$ (c=0.5% in ethanol).

Analysis: $C_{21}H_{32}O_3$: Calculated: % C 75.86, % H 9.70, Found: C 76.0, H 9.9.

EXAMPLE 16

3aβ-methyl-3β-hexanoyloxy-6-ethyl-1,2,3,3a,4,5,8,9-,9a,9b-decahydro-7H-benz(e)-inden-7-one Using the procedure of Example 14, 1 g of 3aβ-methyl-6-ethyl-1,2,3,3a,4,5,8,9,9a,9b-decahydro-7H-benz(e)-inden-3β-ol-7-one and 2 ml of caproic anhydride were reacted to obtain 0.7 g of 3aβ-methyl-3β-hexanoyloxy-6-ethyl-1,2,3,3a,4,5,8,9,9a,9b-decahydro-7H-benz(e)-inden-7-one with a specific rotation of $[\alpha]_D^{25} = -15.5°$ (c=0.5% in ethanol).

Analysis: $C_{22}H_{34}O_3$: Calculated: % C 76.25, % H 9.89, Found: C 76.3, H 9.9.

EXAMPLE 17

3aβ-methyl-3β-(pyridin-3-yl)-carbonyloxy-6-ethyl-1,2,3,3a,4,5,8,9,9a,9b-decahydro-7H-benz(e)-inden-7-one 1.95 g of nicotinic acid chloride hydrochloride were added with stirring under an inert atmosphere to 15 ml of anhydrous pyridine and then 2.48 g of 3aβ-methyl-6-ethyl-1,2,3,3a,4,5,8,9,9a,9b-decahydro-7H-benz(e)-inden-3β-ol-7-one were added to the mixture. The mixture was heated at 90°–95° C. for 2½ hours, was cooled and poured into an ice-water mixture. The mixture was filtered and the product was washed with water and dried. The filtrate was extracted with ethyl acetate and the organic phase was washed with water, dried and evaporated to dryness. The filter product and the residue were combined and chromatographed over silica gel. Elution with a 98-2 chloroform-methanol mixture yielded 2.75 g of 3aβ-methyl-3β-(pyridin-3-yl)-carbonyloxy-6-ethyl-1,2,3,3a,4,5,8,9,9a,9b-decahydro-7H-benz(e)-inden-7-one melting at 134° C. and having a specific rotation of $[\alpha]_D^{25} = +46.5° \pm 2°$ (c=0.75% in ethanol).

Anaylsis: $C_{22}H_{27}NO_3$: Calculated: % C 74.75, % H 7.70, % N 3.96, Found: C 74.9, H 7.8, N 3.9.

EXAMPLE 18

A pomade for cutaneous application was prepared containing 50 mg of the product of Example 3 and sufficient excipient of mineral oil, propylene glycol and petrolatum designed as a mixture of semisolid hydrocarbons obtained from petroleum (See USP.XX) for a final weight of 1 g.

A gel composition was prepared containing 50 mg of the product of Example 3 and sufficient excipient of alcohol, carbopol, propylene glycol, water and diisopropanol amine for a total weight of 1 g.

Gelules were prepared containing 50 mg of the product of Example 3 and sufficient excipient of magnesium stearate, lactose and starch for a final weight of 400 mg.

PHARMACOLOGICAL DATA

In the following tests, product A is 3a$\beta$,6-dimethyl-1,2,3,3a,4,5,8,9,9a,9b-decahydro-7H-benz(e)-inden-3$\beta$-ol-7-one described in Belgium Patent No. 663,197, product B is 3a$\beta$-methyl-6-ethyl-1,2,3,3a,4,5,8,9,9a,9b-decahydro-7-H-benz(e)-inden-3$\beta$-ol-7-one described in French Patent No. 1,359,675 and product C is 3a$\beta$-ethyl-6-methyl-1,2,3,3a,4,5,8,9,9a,9b-decahydro-7H-benz(e)-inden-3$\beta$-ol-7-one described in J. Org. Chem., Vol. 34(1) (1969), P 107-112 and are within the scope of formula I.

A. Measure of interaction with androgen receptor

The prospates of adult male rats weighing 200 g castrated 24 hours earlier were homogenized at 0° C. in a buffered T. S. consisting of 10 mM Tris and 0.25M of saccharose with a pH of 7.4 at a rate of 1 g of prostate per 15 ml of buffered solution. The homogenate was centrifuged at 105,000 g for 60 minutes in an ultracentrifuge and the surnageant was called cytosol. Samples of 125 $\mu$l of cytosol were incubated for 30 minutes or 24 hours at 0° C. in the presence of 5 nM of (3H)-testosterone in the absence (Bo) or in the presence (B) of increasing concentrations of cold test products. After the incubation. 100 $\mu$l of the incubate were stirred with 100 $\mu$l of a suspension of 1.25% of Norit A (carbon) and 0.625% of Dextran T80 for 10 minutes at 0° to 4° C. in a microtiter plate and the mixture was centrifuged at 800 g for 10 minutes at 0° to 4° C. The radioactivity contained in the samples of 100 $\mu$l of surnagent was measured by liquid scintillation and the value of the ratio of B/Bo was graphically represented as a function of concentration of cold product added. The concentration of test product necessary to inhibit by 50% the fixation of (3H)-testosterone or CI$_{50}$ was graphically determined. The ratio $$\frac{CI_{50} \text{ Testosterone}}{CI_{50} \text{ Product}} \times 100$$

gives the affinity value relative to the test product for androgen receptor. Previous studies showed that the relatively affinity for a product diminished when the incubation temperature increased and that the product was deemed a potential antihormone [TIPS, August, 1980, p. 324 and Advances in Parmacology and Therapeutics, Vol. 1 receptors, p. 259 (1979)]. The results are reported Table I.

of 125 $\mu$g per day and per animal of testosterone propionate in 0.2 ml of a sesame oil solution containing 0.5% of benzyl alcohol. One group of animals received also a treatment by topical application of an ethanol solution of the test compound on the right costovertebral organ and the left costovertebral organ received only ethanol. The treatment lasted for 8 days and 24 hours after the last, the costovertebral organs and the prostate were removed and weighed. Control animals received only solvents and the results are reported in Table II.

TABLE II

| Daily Treatments | Control Gland in mg | Treated Gland in mg | Prostate in mg |
|---|---|---|---|
| Controls | 6,3 ± 0,7 | 6,4 ± 0,5 | 17,8 ± 2,7 |
| Testosterone Propionate 0,125 $\mu$g/day | 35,8 ± 5,0 | 33,91 ± 2,9 | 79,5 ± 5,5 |
| Testosterone Propionate 125 $\mu$g/day + Product B 1 mg/day | 41,8 ± 5,2 | 17,1 ± 2,2 | 80,1 ± 9,3 |

Local applications of product B to the right costovertebral organ caused a 61% inhibition in the weight increase of the organ. Product B did not antagonize the effect of testosterone propionate on the untreated gland or the prostate indicating that the compound does not have a systemic effect.

The study was repeated with female hamsters to test the antiandrogenic activity of the compounds of Examples 7 and 13 at a dose of 5 mg/day and the results are reported in Table III.

TABLE III

| Daily Treatment | Control Gland in mg | Treated Gland in mg |
|---|---|---|
| Control | 3,0 ± 0,4 | 3,4 ± 0,4 |
| Testosterone Propionate 0,125 $\mu$g/day | 15,8 ± 1,0 | 14,9 ± 1,1 |
| Testosterone Propionate 0,125 $\mu$g/day + Product of Example 7 5 mg/day | 9,5 ± 0,8 | 4,5 ± 0,4 |
| Testosterone Propionate 0,125 $\mu$g/day + Product of Example 13 5 mg/day | 10,8 ± 2,1 | 3,9 ± 0,4 |

Topical application of the product of Example 7 to the right costovertebral organ caused a 90% inhibition of the weight increase of the organ while the product of Example 13 caused a 95.6% inhibition.

The test was repeated on female hamsters to determine the antiandrogenic activity of the compounds of

TABLE I

| | Product A | Product B | Product C | Product of Ex. 1 | Product of Ex. 2 | Product of Ex. 3 | Product of Ex. 4 | Product of Ex. 12 |
|---|---|---|---|---|---|---|---|---|
| % Relative affinity with 30 minutes incubation | 46 | 7,2 | 11,4 | 7,2 | 17 | 9,7 | 2,3 | 73 |
| % Relative affinity with 24 hours incubation | 4 | 0,8 | 5 | 1,3 | 1,7 | 1,2 | 0,3 | 8,4 |

B. In vivo study with costovertebral organ of hamsters

Male golden hamsters weighing 100 to 110 g castrated 7 days earlier received a subcutaneous injection Examples 13 to 17 at 1 mg/day and the results are reported in Table IV.

TABLE IV

| Daily Treatment | Control Gland in mg | Treated Gland in mg | % inhibition of weight increase |
|---|---|---|---|
| Control | 3,3 ± 0,6 | 3,3 ± 0,6 | |
| Testosterone Propionate 0,125 µg/day | 11,0 ± 2,0 | 10,2 ± 0,6 | |
| Testosterone Propionate + Product of Ex. 13 1 mg/day | 9,9 ± 1,6 | 6,0 ± 0,2 | 61% |
| Testosterone Propionate + Product of Ex. 14 1 mg/day | 8,4 ± 0,7 | 4,9 ± 0,3 | 77% |
| Testosterone Propionate + Product of Ex. 15 1 mg/day | 7,1 ± 1,0 | 5,3 ± 0,6 | 71% |
| Testosterone Propionate + Product of Ex. 16 1 mg/day | 8,5 ± 0,5 | 5,6 ± 0,8 | 67% |
| Testosterone Propionate + Product of Ex. 17 1 mg/day | 9,6 ± 1,1 | 8,2 ± 0,9 | 29% |

C. Acute toxicity

Five male mice weighing 18 to 20 g received an intraperitoneal or oral administration of decreasing doses of product B in aqueous solution containing 0.25% of carboxymethyl cellulose and 0.2% of Tween at 1000, 600 or 400 mg/kg and the number of dead mice was determined on the 7th day. The $DL_o$ or the more elevated dose at which no mortality was observed was determined to be 400 mg/kg intraperitoneally and 1000 mg/kg orally for product B.

Various modifications of the products and processes of the invention may be made without departing from the spirit or scope thereof and it is to be understood that the invention is intended to be limited only as defined in the appended claims.

What is claimed is:

1. A process for the preparation of a compound which has the formula

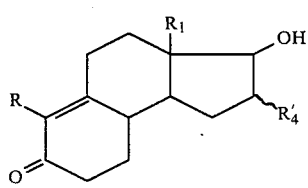

$I_B'$ wherein R is alkyl of 1 to 4 carbon atoms and $R_1$ is methyl or ethyl and $R_4$ is alkyl of 1 to 4 carbon atoms comprising reacting a compound of the formula

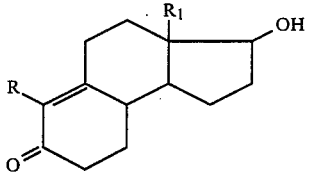

$II_B$ wherein R and $R_1$ have the above definition with a ketone protecting reactant to obtain a compound of the formula

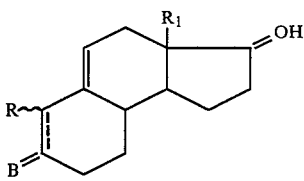

$III_B$ wherein R is a ketal, enamine or enol ether and the dotted line is a double bond when B is an enamine or enol ether, reacting the latter with an oxidation agent selected from the group consisting of pyridinium dichromate, sulfochromic acid solution, pyridinium chlorochormate, chromium trioxide in pyridinium, aluminum isopropoxide and aluminum tertiary butoxide to obtain a compound of the formula

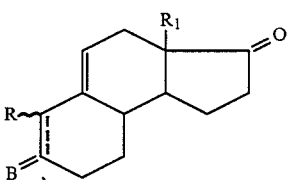

$IV_B$ treating the latter with an iodide of the formula $R_4 I$ in the presence of a strong base to form a compound of the formula

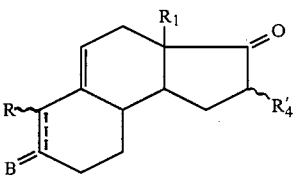

$V_B$ reacting the latter with a reducing agent selected from the group consisting of lithium aluminum hydride, sodium borohydride, potassium borohydride, and lithium borohydride to obtain a compound of the formula

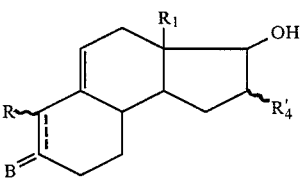

$V_B'$ and treating the latter to remove the ketone protecting group to obtain the compound of formula $I_B$.

2. A process for the preparation of a compound which has the formula

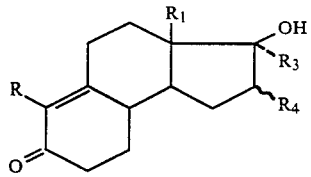

wherein R is alkyl of 1 to 4 carbon atoms, $R_1$ is methyl or ethyl, $R_3$ is selected from the group consisting of hydrogen, alkyl of 1 to 4 carbon atoms and alkenyl and alkynyl of 2 to 4 carbon atoms, $R_4$ is selected from the group consisting of hydrogen and alkyl of 1 to 4 carbon atoms, with the proviso that when $R_4$ is hydrogen, R and $R_1$ are not methyl when $R_3$ is ethyl comprising reacting a compound of the formula

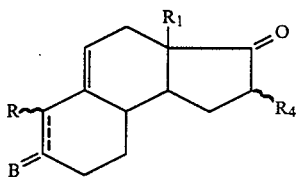

wherein B, R, $R_1$, $R_4$ and the dotted line have the above definition with a compound of the formula $R_3$-D wherein $R_3$ has the above definition and D is lithium or Mg-Hal and Hal is a halogen to obtain a compound of the formula

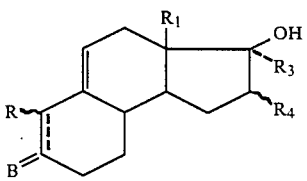

and treating the latter to remove the ketone protecting group to obtain the compound of formula $I_C$.

3. A process for the preparation of a compound which has the formula

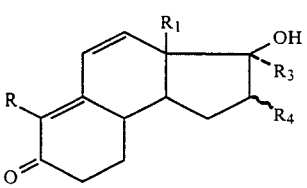

wherein R is alkyl 1 to 4 carbon atoms, $R_1$ is methyl or ethyl, $R_3$ is selected from the group consisting of hydrogen, alkyl of 1 to 4 carbon atoms and alkenyl and alkynyl of 2 to 4 carbon atoms, $R_4$ is selected from the group consisting of hydrogen and alkyl of 1 to 4 carbon atoms, comprising reacting a compound of the formula

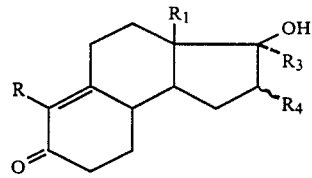

with a hydroxyl protecting reactant to obtain a compound of the formula

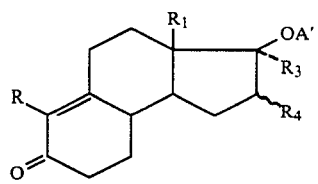

wherein A' is a hydroxyl protecting group, reacting the latter with a brominating agent to obtain a compound of the formula

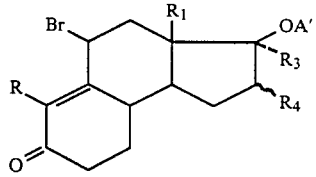

and treating the latter with a dehydrobromination agent and an agent to remove the hydroxyl protecting group to obtain a compound of formula $I_D$.

4. A process for the preparation of a compound which has the formula

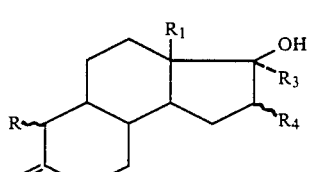

wherein R is alkyl of 1 to 4 carbon atoms and $R_1$ is methyl or ethyl, $R_3$ is selected from the group consisting of hydrogen, alkyl of 1 to 4 carbon atoms and alkenyl and alkynyl of 2 to 4 carbon atoms, $R_4$ is selected from the group consisting of hydrogen and alkyl of 1 to 4 carbon atoms with the proviso that when $R_4$ is hydrogen, (a) R and $R_1$ are not methyl when $R_3$ is hydrogen, methyl, ethyl, propargyl or isobutenyl or (b) when $R_3$ is hydrogen, R is not methyl and $R_1$ is ethyl or $R_1$ is methyl and R is not ethyl comprises reacting a compound of the formula

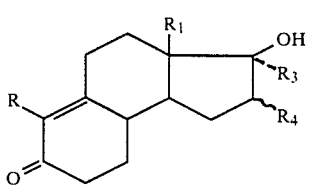

with a hydrogenation agent to obtain the compound of formula $I_E'$.

5. A process for the preparation of a compound which has the formula

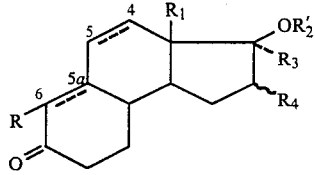

$I_F'$ wherein R is alkyl of 1 to 4 carbon atoms, $R_1$ is methyl or ethyl, $R_3$ is selected from the group consisting of hydrogen, alkyl of 1 to 4 carbon atoms and alkenyl and alkynyl of 2 to 4 carbon atoms, $R_4$ is selected from the group consisting of hydrogen and alkyl of 1 to 4 carbon atoms and $R_2'$ is $R_2$ other than hydrogen excluding the compounds wherein $R_4$ is hydrogen, the dotted line in the 4(5)-position is not a double bond and the dotted line in the 5a(6)-position is a double bond and (a) R is methyl, $R_3$ is hydrogen and (i) $R_2'$ is acetyl, tert.-butyl or benzoyl and $R_1$ is methyl or (ii) $R_2'$ is tert.-butyl and $R_1$ is ethyl, (b) R is ethyl or propyl, $R_3$ is hydrogen, $R_2'$ is benzoyl and $R_1$ is methyl and excluding also the compounds wherein $R_4$ is hydrogen and the dotted lines do not indicate a double bond and (a) $R_1$ and R are methyl, $R_3$ is hydrogen and $R_2'$ is acetyl or benzoyl, (b) R and $R_1$ are methyl, $R_2'$ is methoxymethyl and $R_3$ is hydrogen and (c) R, $R_1$ and $R_3$ are methyl and $R_2'$ is acetyl comprising either reacting a compound of the formula

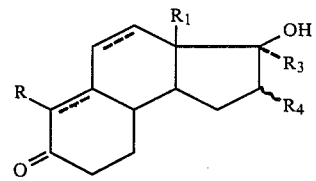

$II_F$ with a compound of the formula $R_2'$-E wherein E is a functional group residue and $R_2'$ has the above definition to obtain the corresponding compound of formula $I_F'$ or reacting a compound of the formula

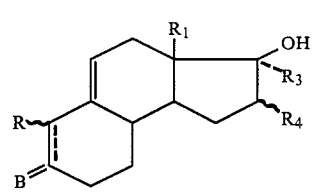

$II_F'$ wherein B has the above definition with a compound of the formula $R_2'$-E wherein $R_2'$ and E have the above definition to obtain a compound of the formula

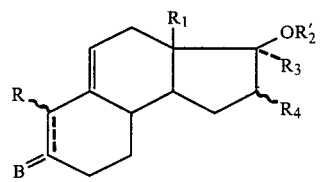

$III_F'$ and treating the latter to remove the ketone protecting group to obtain a compound of formula $I_F'$ wherein there is no double bond in the 4(5)-position.

* * * * *